United States Patent
Kim et al.

(10) Patent No.: US 7,544,967 B2
(45) Date of Patent: Jun. 9, 2009

(54) LOW VOLTAGE FLEXIBLE ORGANIC/TRANSPARENT TRANSISTOR FOR SELECTIVE GAS SENSING, PHOTODETECTING AND CMOS DEVICE APPLICATIONS

(75) Inventors: Il-Doo Kim, Seoul (KR); Harry L. Tuller, Wellesley, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 179 days.

(21) Appl. No.: 11/391,120

(22) Filed: Mar. 28, 2006

(65) Prior Publication Data

US 2006/0231882 A1 Oct. 19, 2006

Related U.S. Application Data

(60) Provisional application No. 60/665,751, filed on Mar. 28, 2005.

(51) Int. Cl.
*H01L 35/24* (2006.01)
*H01L 51/00* (2006.01)

(52) U.S. Cl. .................. 257/40; 257/289; 257/295; 257/296; 257/E21.272; 257/E21.274; 438/99; 438/396; 438/591

(58) Field of Classification Search .......... 257/40, 257/289, 295, 296; 438/99, 591
See application file for complete search history.

(56) References Cited

U.S. PATENT DOCUMENTS

| | | | |
|---|---|---|---|
| 6,207,472 B1 * | 3/2001 | Callegari et al. ............. 438/99 |
| 6,344,660 B1 * | 2/2002 | Dimitrakopoulos et al. ... 257/40 |
| 6,344,662 B1 * | 2/2002 | Dimitrakopoulos et al. ... 257/40 |
| 6,482,527 B1 * | 11/2002 | Shrout et al. ................ 428/469 |
| 6,575,013 B2 | 6/2003 | Bao et al. |
| 6,914,279 B2 | 7/2005 | Lu et al. |
| 2001/0015438 A1 | 8/2001 | Callegari et al. |
| 2001/0048489 A1 | 12/2001 | Izumi et al. |
| 2006/0076584 A1 * | 4/2006 | Kim et al. ................... 257/275 |
| 2006/0108579 A1 * | 5/2006 | Kim et al. ................... 257/40 |

OTHER PUBLICATIONS

Torsi et al., "Alkoxy-substitute polyterthiophene thin-film-transistors as alcohol sensors" 2003 Elsevier, Sensors & Actuators B 98 (2004) 204-207.

Ryu et al., "ZnO devices: Photodiodes and p-type field-effect transistors" Applied Physics Letters, 87 (2005) 153504-153504-3.

Batista et al., "ZnO extended-gate filed-effect transistors as pH sensors" Applied Physics Letters, 87 (2005) 143508-143508-3.

Bae et al., "Dynamic and static photoresponse of ultraviolet-detecting thin-film transistors based on transparent Niox electrodes and N-ZnO channel" Journal of Applied Physics 97 (2005) 076104-076104-3.

(Continued)

*Primary Examiner*—Dao H Nguyen
(74) *Attorney, Agent, or Firm*—Gauthier & Connors LLP

(57) ABSTRACT

A thin film transistor (TFT) includes a source electrode, a drain electrode, and a gate electrode. A gate insulator is coupled to the source electrode, drain electrode, and gate electrode. The gate insulator includes room temperature deposited high-K materials so as to allow said thin film transistor to operate at low operating voltage.

20 Claims, 4 Drawing Sheets

OTHER PUBLICATIONS

Bae et al., Photodetecting properties of ZnO-based thin-film transistors, Applied Physics Letters vol. 83, No. 25 (2003) 5313-5315.

Fukuda et al., "Gas sensors based on poly-3-hexylthiophene thin-film transistors" Elsevier, Thin Solid Films 464-465 (2004) 441-444.

Wang et al., "Influence of measuring environment on the electrical characteristics of pentacene-based thin film transistors" Elsevier, Thin Solid Films 467 (2004) 215-219.

Presley et al., "Tin oxide transparent thin-film transistors" Journal of Physics D: Applied Physics 37 (2004) 2810-2813.

Bartic et al., "monitoring pH with organic-based filed-effect transistors" Elsevier, Sensors and Actuators B 83 (2002) 115-122.

Hong et al., "Voltage tunable dielectric properties of rf sputtered Bi2O3-ZnO-Nb2O5 pyrochlore thin films" Elsevier, Thin Solid Films, 419, 2002, pp. 183-188.

Kang et al., "Mn-doped Ba0.6Sr 0.4TiO3 high-K gate dielectrics for low voltage organic transistor on polymer substrate" Applied Physics Letters, 87, pp. 242908-1-242098-3 (2005).

Choi et al., "Low-Voltage Organic Transistors and Depletion-Load Inverters With High-K PyrochloreBZN Gate Dielectric on Polymer Substrates" IEEE Transactions on Electron Devices, vol. 52, No. 12, Dec. 2005, pp. 2819-2824

* cited by examiner

LOW VOLTAGE FLEXIBLE ORGANIC/TRANSPARENT TRANSISTOR FOR SELECTIVE GAS SENSING, PHOTODETECTING AND CMOS DEVICE APPLICATIONS

PRIORITY INFORMATION

This application claims priority from provisional application Ser. No. 60/665,751 filed Mar. 28, 2005, which is incorporated herein by reference in its entirety.

BACKGROUND OF THE INVENTION

The invention relates to the field of transistors, and in particular to a thin film transistor (TFT) having high-K gate dielectrics.

Thin film transistor (TFT) technology on plastic substrates offers many potential advantages not only with respect to displays but also to wide area digital logic circuitry, electronic-paper and books, wearable electronics, sensors, photodetectors, actuators. Room temperature fabricated Organic-TFTs (OTFTs) and ZnO-based transparent-TFTs can contribute to reduced cost by substituting inexpensive plastic substrates for relatively high cost Si wafers or flat glass substrates utilized today.

TFT-type sensors are undoubtedly of great importance for the development of microelectronics-based smart sensing systems. Several parameters of hybrid OTFT (organic thin film transistors)/Metal-Oxide TFT (semiconducting metal-oxide thin film transistors) such as saturation current, on/off current, threshold voltage, and sub-threshold voltage slope can vary in response to various gases and volatile organic compounds. Advantages of TFT-based sensors include high sensitivity and selectivity, resulting from special features of organics e.g. their specialized bonding sites, coupled with the ability to use flexible substrates and low temperature processing leading to low manufacturing costs. In order to form electronic noses (e-noses), which are designed to detect and distinguish between many complex odors, large arrays of sensors are required. While this can be done in principle with other types of sensors such as SAW (surface acoustic wave) devices, quartz crystal microbalances (QCM), organic/inorganic resistors, their size and complexity often make this impractical. The ability to assemble gas sensitive TFTs into large arrays is therefore an important feature.

Such TFT-type sensors benefit by ease of integration with associated transducer or signal processing circuitry, as well as, into fabrics. Also, the development of ultra low-power TFT compatible gas sensor arrays can be a key component for further technologies. To date, the operating voltages, between 10 and 100 V, of TFTs with low-K gate dielectrics on plastic substrate are commonly too high, especially for portable, battery-powered sensing device applications, e.g. medical monitoring and/or toxic chemical sensors integrated within military uniforms.

ZnO is also known to have the capacity to detect ultraviolet (UV) photons. ZnO-based TFTs can be used for photodetecting elements. Photodetecting devices with low cost and low voltage operation (<5V) will have benefits. High-K gate oxide growth by a near room temperature process on glass or plastic substrates is essential.

Another interesting application area utilizes CMOS technology based on a combination of OTFT (organic thin film transistors)/Metal-Oxide TFT (semiconducting metal-oxide thin film transistors) with p-channel and n-channel as active channels, respectively. Pentacene is a well studied p-type semiconductor material. Undoped zinc oxide (ZnO) has an electron channel mobility which can support high drive currents and fast operating speeds. Alternatively, InGaO$_3$, with field effect mobility of 80 cm$^2$/Vs, could be used instead of ZnO.

SUMMARY OF THE INVENTION

According to one aspect of the invention, there is provided a thin film transistor (TFT). The TFT includes a source electrode, a drain electrode, and a gate electrode. A gate dielectric is coupled to the source electrode, drain electrode, and gate electrode. The gate insulator includes room temperature deposited high-K materials so as to allow said thin film transistor to operate at low voltage.

According to another aspect of the invention, there is provided a method of forming a thin film transistor (TFT). The method includes forming a source electrode, a drain electrode, and a gate electrode. Also, the method includes forming a gate dielectric that is coupled to the source electrode, drain electrode, and gate electrode. The gate insulator includes room temperature deposited high-K materials so as to allow said thin film transistor to operate at low operating voltage.

DETAILED DESCRIPTION OF THE INVENTION

By introducing High-K gate dielectrics, one can successfully reduce the operating voltages for TFTs sensors, photodetectors, and CMOS circuits. The invention utilizes the high K-dielectric Bi$_{1.5}$Zn$_{1.0}$Nb$_{1.5}$O$_7$ (BZN series, A$_2$B$_2$O$_7$ pyrochlore structure materials) with relative dielectric constants of 50-55 depending on growth method. High-K BZN films can be deposited by sputtering, pulsed laser deposition, chemical vapor deposition method, spray drying with nanoparticle incorporation, printing techniques, or other techniques.

Figure 1A:
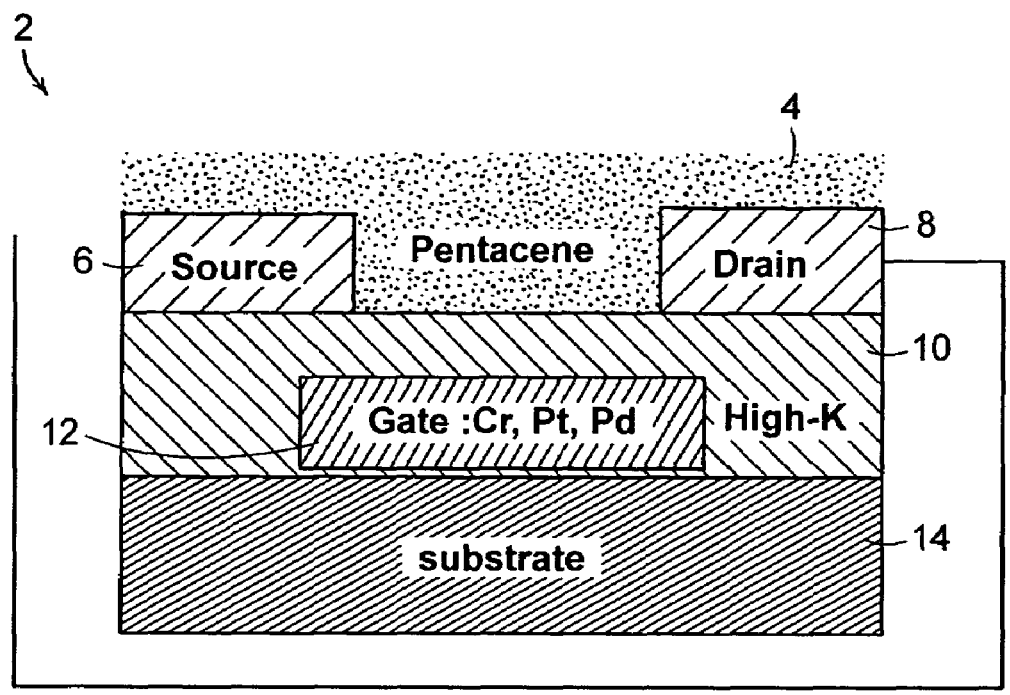
FIGS. 1A-1B are schematic diagrams of an organic thin films transistor (TFT) sensors formed in accordance with the invention.
Figure 1B:
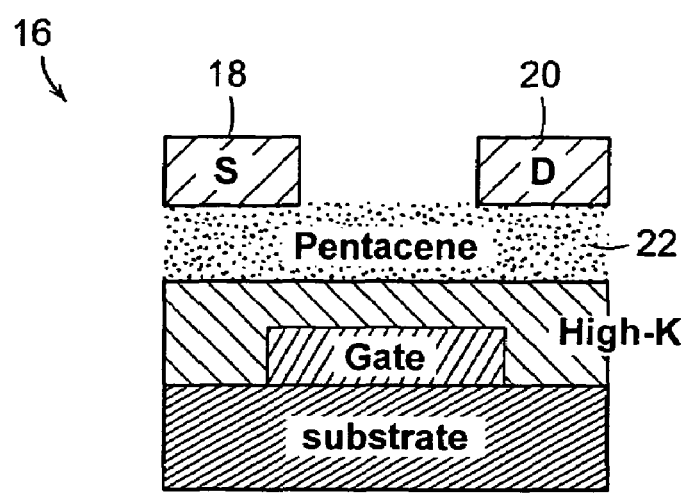

The invention provides an environment for which both organic and inorganic transistors having high-K gate dielectrics can be used. First, the organic thin film transistor (OTFT) includes a semiconductor layer comprising pentacene, however in other embodiments, conjugated polymers such as poly-3-alkykthiophene, poly-3-hexylthiophene (P3HT), poly-thienlylene vinylene or tetracene can be used as the semiconductor layer. FIGS. 1A-1B are schematic diagrams of bottom and top contact OTFT sensors. The semiconductor layer 4 is exposed to various gases for sensing. The response differs with various gases in each case depending on the different charge induced in the organic semiconductor channel (as commonly understood in FET terminology, that being the conductive channel allowing for charge transport between source and drain), as shown in FIG. 1A.

The resistivity of semiconductor layer 4 is changed when it was exposed to the gases for sensing. In the embodiment 50 shown in FIG. 1A, the semiconductor layer 4 is pentacene, however, other materials can be used having similar properties. A source electrode 6 and drain electrode 8 are formed on a high-K gate insulator layer 10 before the semiconductor layer 4 is deposited. As described above, the high-K dielectric layer 10 can include $Bi_{1.5}Zn_{1.0}Nb_{1.5}O_7$ (BZN series, $A_2B_2O_7$ pyrochlore structure materials) or the like. A gate electrode 12 is formed in a selective region in the high-K gate dielectric 10. The gate electrode 12 can include materials such as Cr, Pt, Pd, or the like. Both the gate electrode 12 and gate insulator 10 are formed on a substrate 14. In other embodiments, the substrate 14 can be plastic, polymide or a glass substrate.

FIG. 1B illustrates another embodiment 52 of the invention. This OTFT sensor 16 is substantially similar to the structure 2 described in FIG. 1A except the source electrode 18 and drain electrode 20 are formed on a semiconductor layer 22. The semiconductor layer 22 is exposed to various gases for sensing but a portion is maintained to allow for an active channel. Note in this embodiment, the semiconductor layer 22 is pentacene, however, other materials having similar properties can be used.

Figure 2:
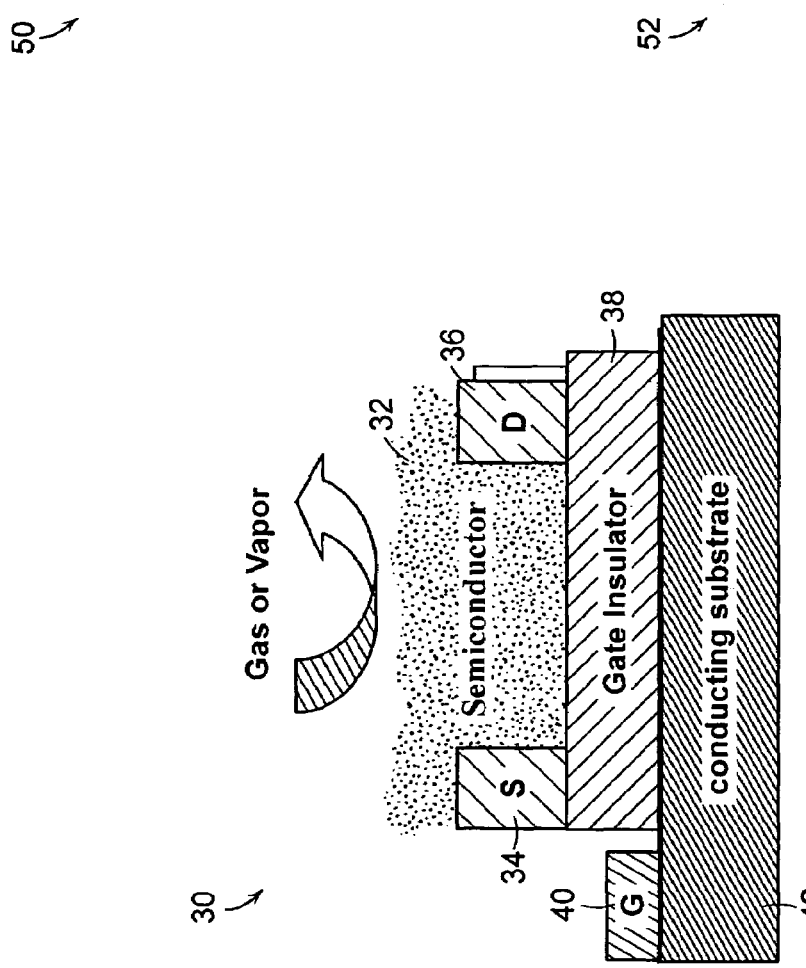
FIG. 2 is a schematic diagram of a semiconducting metal-oxide thin film transistor (TFT) sensor formed in accordance with the invention.

FIG. 2 illustrates a semiconducting metal-oxide thin film transistor (Metal-Oxide TFT) sensor 30 formed in accordance of the invention. The metal-oxide thin film transistor 30 sensor includes an inorganic semiconductor layer 32 comprising ZnO, however in other embodiments, $TiO_2$, $SnO_2$, $In_2O_3$ or the like can be used as the semiconductor layer 32. The semiconductor layer 32 is exposed to various gases such as $H_2$, $NO_2$, CO, $CO_2$, $NH_3$, DMMP or the like for sensing. The response differs with various gases in each case depending on the different charge induced in the inorganic semiconductor channel.

The resistivity of semiconductor layer 32 is changed when it is exposed to the gases for sensing. A source electrode 34 and drain electrode 36 are formed on a high-K gate insulator layer 38 before the semiconductor layer 32 is deposited. The high-K insulator layer 38 can include $Bi_{1.5}Zn_{1.0}Nb_{1.5}O_7$ (BZN series, $A_2B_2O_7$ pyrochlore structure materials) or the like. A gate electrode 40 is formed in a selective region away from the high-K gate dielectric layer 38. The gate 40 can include catalyst metals such as Poly-Si, Al, Cr, Ni, Pt, Pd, ITO, TiN, and W. Both the gate 40 and high-K gate dielectric 38 are formed on a conductive substrate 42.

The semiconductor layer can act as both an active channel and sensing material. The ZnO is n-type transparent oxide semiconductor. When different gases, such as combustible gases, or permanent gases, are exposed to these semiconductor materials, the transistor performance changes depending on the gas, temperature, semiconductor layer, and the catalyst metal used. Moreover, thin catalyst metals can be deposited on top of the organic/inorganic semiconductor layers to increase surface activity with care taken to insure that no conductive pathway is provided via the catalyst metal particles.

The invention provides an accurate and sustainable way to produce viable CMOS circuits utilizing p-type and n-type TFT materials.

Figure 3A:
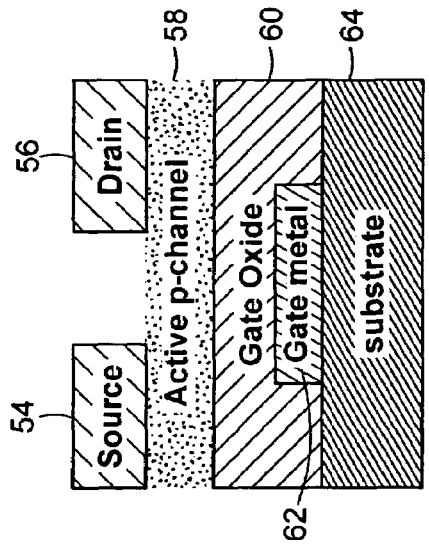
FIGS. 3A-3B are schematic diagrams illustrating an exemplary embodiment of the invention wherein a p-type and n-type TFT structures are formed in accordance with the invention.
Figure 3B:
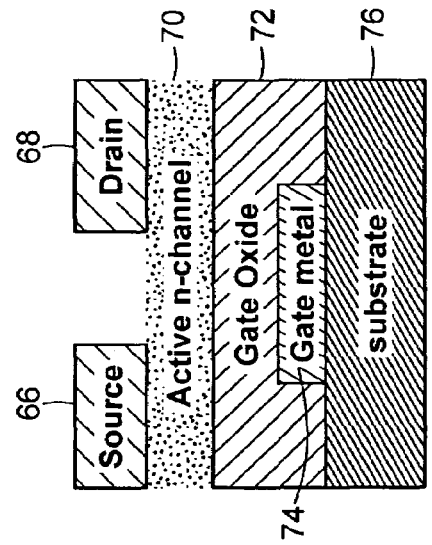

FIGS. 3A-3B illustrates an embodiment of the invention wherein a p-type and n-type TFT structures 50, 52 are formed in accordance with the invention. In particular, FIG. 3A shows a p-type TFT structure 50 that includes a source 54 and drain 56 that are formed on an active p-channel 58. The active p-channel 58 is formed on a gate oxide 60 a portion of which covers a gate metal 62. Both the gate oxide 60 and the gate metal 62 are formed on a substrate 64. The active p-channel 58 can include pentacene, conjugated polymer such as poly-3-alkykthiophene, poly-3-hexylthiophene (P3HT), poly-thienlylene vinylene or tetracene. The gate oxide 60 can include high-K BZN, Mn/Ni doped $(Ba,Sr)TiO_3$ (BST), hybrid structures—Mn/Ni doped BST/BZN or the like. The substrate 64 can include any kind of plastic substrate such as polyimide, PEN, PET, polycarbonate fabrics, Si substrate, glass substrate or the like.

FIG. 3B shows an n-type TFT 52 that includes a source 66 and drain 68 that are formed on an active n-channel 70. The active n-channel 70 is formed on a gate oxide 72, a portion of which covers a gate metal 74. Both the gate oxide 72 and the gate 74 metal are formed on a substrate 76. The active n-channel 70 can include ZnO, $In_{1-x}Ga_xZnO$ (IGZO), $SnO_2$, or the like. The gate oxide 72 can include high-K BZN, Mn/Ni doped $(Ba,Sr)TiO_3$, hybrid structures—Mn/Ni doped BST/BZN or the like. The substrate 76 can include any kind of plastic substrate such as polyimide, PEN, PET, polycarbonate fabrics, Si substrate, glass substrate or the like.

The OTFT threshold voltage can be controlled by deposition of a thin parylene layer or a thin inorganic layer such as room temperature grown MgO and $Al_2O_3$ at the interface of the BZN gate oxide and the pentacene semiconductor. By the combination of n-channel TFTs and p-channel TFTs with different and controllable threshold voltages, one can fabricate and develop a wide range of logic circuits and macroelectronics on glass and flexible substrates.

Other very thin inorganic films having thicknesses between 0.1 nm and 30 nm, such as room temperature sputtered YSZ (yttrium-stabilized zirconia), $CeO_2$, $Y_2O_3$, $Al_2O_3$, $HfO_2$, $SrTiO_3$, $LaAlO_3$, $MgAl_2O_4$ on BZN, Ni or Mn doped BST films, can be used for the manipulation of threshold voltage. These stacked, thin covered layer/BZN, structures will provide enhancement mode and depletion mode circuits to complete various digital logic circuits such as NAND, inverter, ring oscillator, various memory devices and micro-arrayed CMOS for sensor and photodectector applications.

Using the same concepts described herein for p-type and n-type TFTs to form CMOS circuits, one can also formulate other thin film transistor (TFT) sensors and photodetectors. These structures can include a gate oxide having BZN and other pyrochlore structured series or perovskite structured 0.1~5% Ni or Mn doped $(Ba,Sr)TiO_3$ (BST), The pyrochlore structured series films, having a thickness between 50 nm and 500 nm, can include $(Bi_{1.5}Zn_{1.0}Nb_{1.5}O_7, Bi_2(Zn_{1/3}Nb_{2/3})_2O_7, (Bi)_{1-2}(Zn,Nb,Ta,Ti)_2O_7), (Ca, Ba, Sr, Pb) (Zn, Nb, Ta, Ti, Zr)_2O_7, (Ca_{1-x}Sr_x)Bi_4Ti_4O_{15}$. The other gate oxides with perovskite structure can include 2% Ni-doped BST and 3% Mn-doped BST. The doping concentration of Mn and Ni can range from 0.1 to 5%. In order to reduce leakage current, very thin MgO or $Al_2O_3$ layers, having between 1 nm and 10 nm thickness, can be used to coat the above high-K gate oxides. Otherwise, annealing is sometimes desirable (<200° C.) following gate oxide room temperature deposition to further reduce leakage current.

Figure 4A:
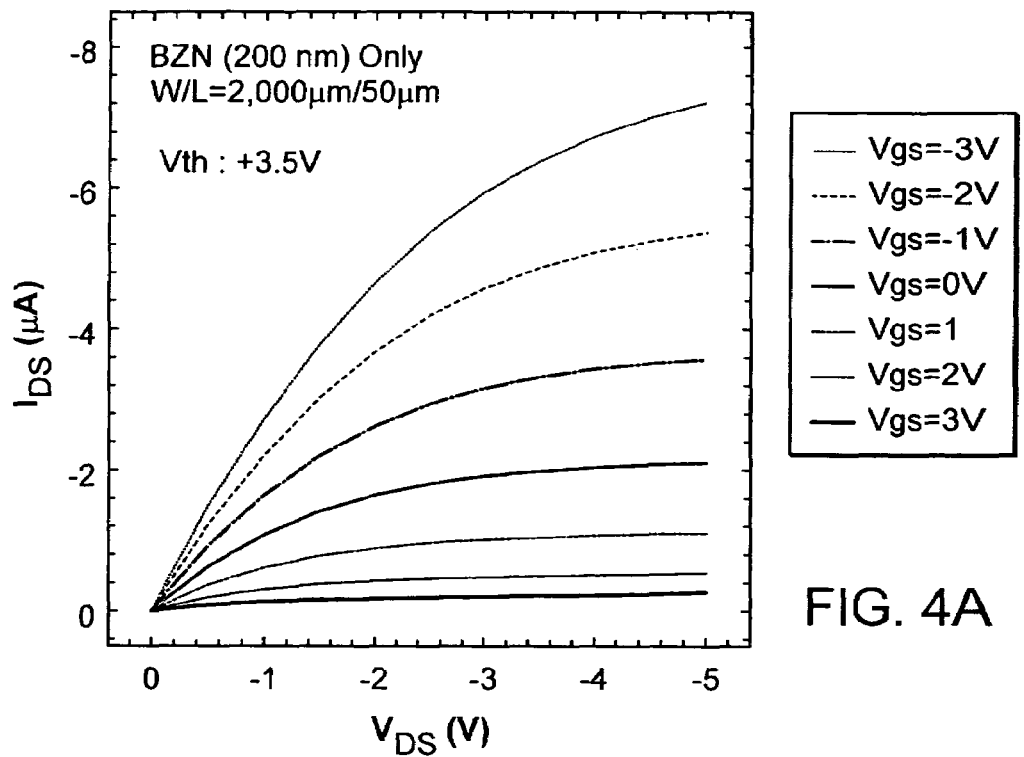
FIGS. 4A-4B are graph demonstrating the operating characteristics of the invention.
Figure 4B:
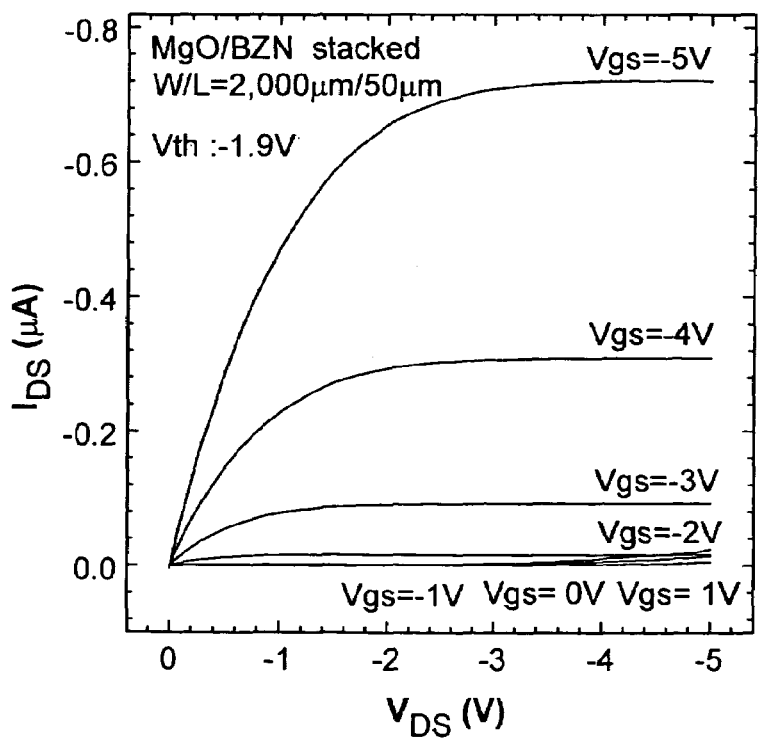

FIGS. 4A-4B shows when using inorganic films such as MgO onto a BZN gate oxide, there is a shift in threshold voltage. As shown in FIG. 4A, the derived values for $V_{th}$ and $\mu_{FE}$ were +3.5 V and 0.13 $cm^2/Vs$ respectively, for pentacene TFTs with BZN gate insulator. The TFTs with stacked MgO/BZN gate oxides showed excellent saturation with low operating voltage of 5 V as shown in FIG. 4B. $V_{th}$ and $\mu_{FE}$ were −1.9 V and 0.053 $cm^2/Vs$ respectively. The threshold voltage of the TFTs was shifted from +3.5V to −1.9 V by inserting the MgO layer between the BZN and pentacene films.

Figure 5A:
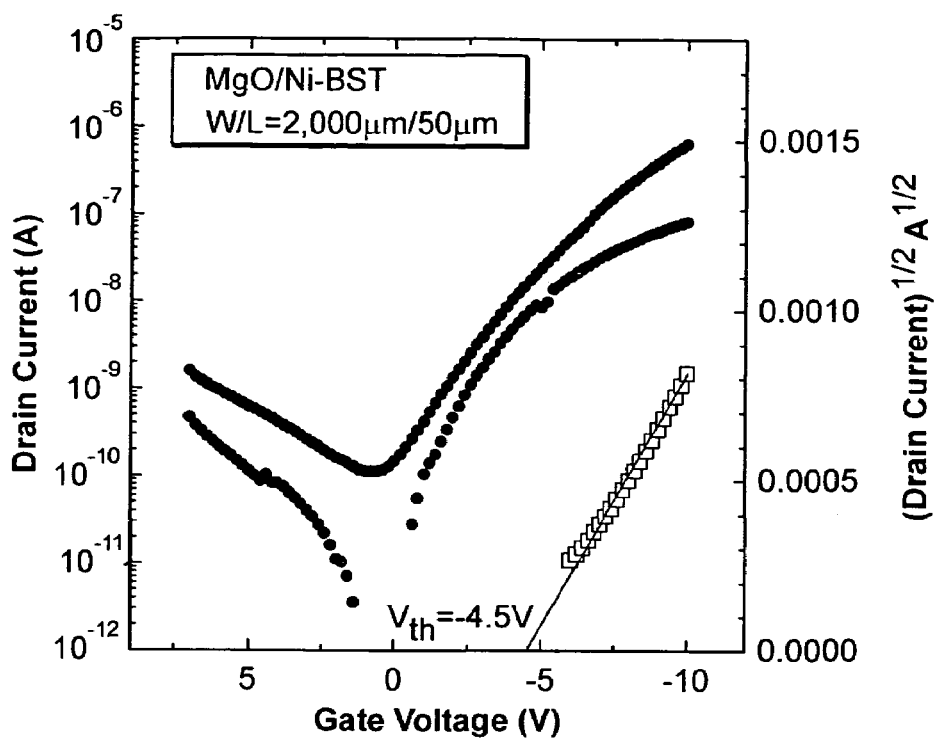
FIGS. 5A-5B are graph demonstrating the operating characteristics of the invention.
Figure 5B:
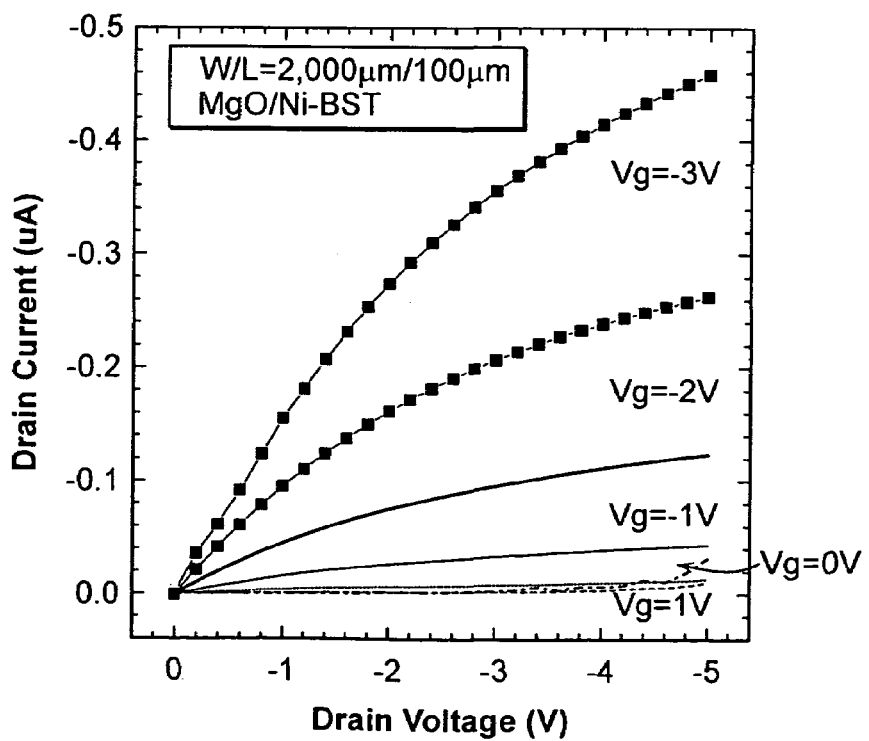

As other example, FIG. 5A-5B shows when using inorganic films such as MgO onto a Ni-doped BST gate oxide, there is also a shift in threshold voltage. As shown in FIG. 5A, the threshold voltage of the TFTs was −4.5 V by inserting the MgO layer between the 5% Ni-doped BST and pentacene films as compared to TFTs with Ni doped BZN only gate oxides which showed $V_{th}$ of +0.8 V. FIG. 5B shows low voltage operation of TFTs by using high-K 5% Ni-doepd BST films. Based on the above results, the threshold voltage can be manipulated for the application of various logic circuits and CMOS.

Although the present invention has been shown and described with respect to several preferred embodiments thereof, various changes, omissions and additions to the form and detail thereof, may be made therein, without departing from the spirit and scope of the invention.

What is claimed is:

1. A low voltage operating thin film transistor (TFT) structure comprising:
   a source electrode;
   a drain electrode;
   a gate electrode; and
   a gate insulator that is coupled to said source electrode, drain electrode, and gate electrode, said gate insulator completely surrounds said gate electrode with room temperature deposited high-K materials so as to allow said thin film transistor to operate at low operating voltage, said gate insulator comprises amorphous or partially nanocrystalline films having at least one material selected from the group consisting of $Bi_{1.5}Zn_{1.0}M_{1.5}O_7$ (M=Ta, Sb), or 0.1~5% Ni, Mg, or Mn doped $(Ba_{1-x}Sr_x)TiO_3$ at room temperature.

2. The TFT structure of claim 1 further comprising a plastic substrate such as PET, PEN, PES, or polyimide that is supported said gate electrode.

3. The TFT structure of claim 1 further comprising a semiconductor layer that is coupled to said source electrode, drain electrode and said gate insulator.

4. The TFT structure of claim 3, wherein said semiconductor layer comprises pentacene, poly-3-alkykthiophene, poly-3-hexylthiophene (P3HT), poly-thienlylene vinylene or tetracene.

5. The TFT structure of claim 3, wherein said semiconductor layer comprises ZnO, $In_2O_3$, $TiO_2$, or $SnO_2$.

6. The TFT structure of claim 3, wherein the semiconductor layer is deposited at room temperature by RF magnetron sputtering.

7. The TFT structure of claim 1, wherein the high-K insulator layer comprising room temperature RF sputtered inorganic films such as very thin (0.1 nm~30 nm) MgO, YSZ (yttrium-stabilized zirconia), $CeO_2$, $Y_2O_3$, $Al_2O_3$, $HfO_2$, $SrTiO_3$, $LaAlO_3$, $MgAl_2O_4$ deposited on the high-K films to manipulate threshold voltage to fabricate enhancement or depletion mode TFTs for use in CMOS application.

8. The TFT structure of claim 1, wherein said gate electrode comprises a catalyst metal.

9. The TFT structure of claim 8, wherein said catalyst metal comprises Poly-Si, Al, Cr, Ni, Pt, Pd, Au, ITO, TiN, or W.

10. The TFT structure of claim 8, wherein said gate electrode is formed in a region interior of said gate dielectric.

11. The TFT structure of claim 8, wherein said gate electrode is formed in a region exterior of said gate dielectric.

12. A method of forming a thin film transistor (TFT) structure comprising:
    forming a source electrode;
    forming a drain electrode;
    forming a gate electrode; and
    forming a gate insulator that is coupled to source electrode, drain electrode, and gate electrode, said gate insulator completely surrounds said gate electrode with room temperature deposited high-K materials so as to allow said thin film transistor to operate at low operating voltages, said gate insulator comprises amorphous or partially nano crystalline films having at least one material selected from the group consisting of $Bi_{1.5}Zn_{1.0}M_{1.5}O_7$ (M=Ta, Sb), or 0.1~5% Ni, Mg, or Mn doped $(Ba_{1-x}Sr_x)TiO_3$ at room temperature.

13. The method of claim 12 further comprising providing a plastic substrate such as PET, PEN, PES, or polyimide that is supported by said gate electrode.

14. The method of claim 12 further comprising forming a semiconductor layer that is coupled to said source, drain electrode and said gate insulator.

15. The method of claim 14, wherein said semiconductor layer comprises pentacene, poly-3-alkykthiophene, poly-3-hexylthiophene (P3HT), poly-thienylene vinylene or tetracene.

16. The method of claim 14, wherein said semiconductor layer comprises ZnO, $In_{1-x}Ga_xZnO$ (IGZO), or $SnO_2$.

17. The method of claim 12, wherein said gate electrode comprises a catalyst metal.

18. The method of claim 17, wherein said catalyst metal comprises Poly-Si, Al, Cr, Ni, Pt, Pd, Au, ITO, TiN, or W.

19. The method of claim 17, wherein said gate electrode is formed in a region interior of said gate dielectric.

20. The method of claim 17, wherein said gate electrode is formed in a region exterior of said gate dielectric.

* * * * *